US00PP24024P3

(12) United States Plant Patent
Blom

(10) Patent No.: US PP24,024 P3
(45) Date of Patent: Nov. 12, 2013

(54) ***CHRYSANTHEMUM* PLANT NAMED 'ZANMUAVAL PURPLE'**

(50) Latin Name: ***Chrysanthemum×morifolium* Ramat.**
Varietal Denomination: Zanmuaval Purple

(75) Inventor: Wilhelmus Bernardus Blom, Leimuiden (NL)

(73) Assignee: Chrysanthemum Breeders Association Research B.V., Aalsmeer (NL)

( * ) Notice: Subject to any disclaimer, the term of this patent is extended or adjusted under 35 U.S.C. 154(b) by 95 days.

(21) Appl. No.: 13/385,347

(22) Filed: Feb. 15, 2012

(65) Prior Publication Data

US 2013/0212758 P1 Aug. 15, 2013

(51) Int. Cl.
*A01H 5/00* (2006.01)

(52) U.S. Cl.
USPC ..... Plt./286

(58) Field of Classification Search
USPC ..... Plt./286
See application file for complete search history.

*Primary Examiner* — Annette Para

(74) *Attorney, Agent, or Firm* — Steptoe & Johnson LLP

(57) ABSTRACT

A *chrysanthemum* plant named 'Zanmuaval Purple' characterized by its medium sized blooms with dark purple ray florets and prolific branching; natural season flower date week 42; blooming for a period of five weeks.

3 Drawing Sheets

Botanical designation: *Chrysanthemum×morifolium* Ramat.

Cultivar denomination: 'Zanmuaval Purple'.

RELATED CULTIVARS

The new plant is a mutant obtained from the *chrysanthemum* plant 'Zanmuaval' (U.S. Plant Pat. No. 22,659).

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmuaval Purple'. The new plant is a product of a breeding and selection program which had the objective of finding color mutants from existing parent plants. The new plant comprises a whole plant mutant of the *chrysanthemum* plant named 'Zanmuaval' Plants from the new cultivar 'Zanmuaval Purple' differ from plants of the parent in the color of the ray-florets. The ray-florets of the mutant plant are more dark purple than those of the parent plant.

The new cultivar was discovered as a color mutant in April 2010 by Wilhelmus Bernardus Blom in a controlled environment (greenhouse) in Rijsenhout, The Netherlands. The first act of asexual reproduction of 'Zanmuaval Purple' was accomplished when after planting of the mutant as a mother-plant in May 2010, vegetative cuttings from this mutant were taken and propagated further in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
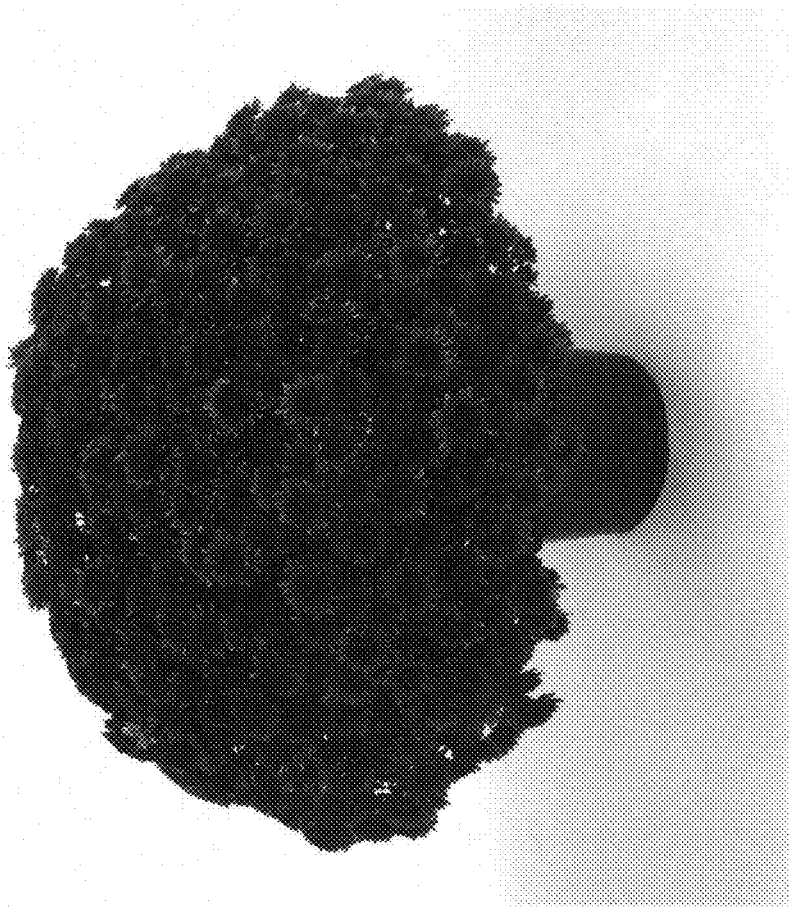
FIG. 1 shows a plant of the cultivar in full bloom.
Figure 2:
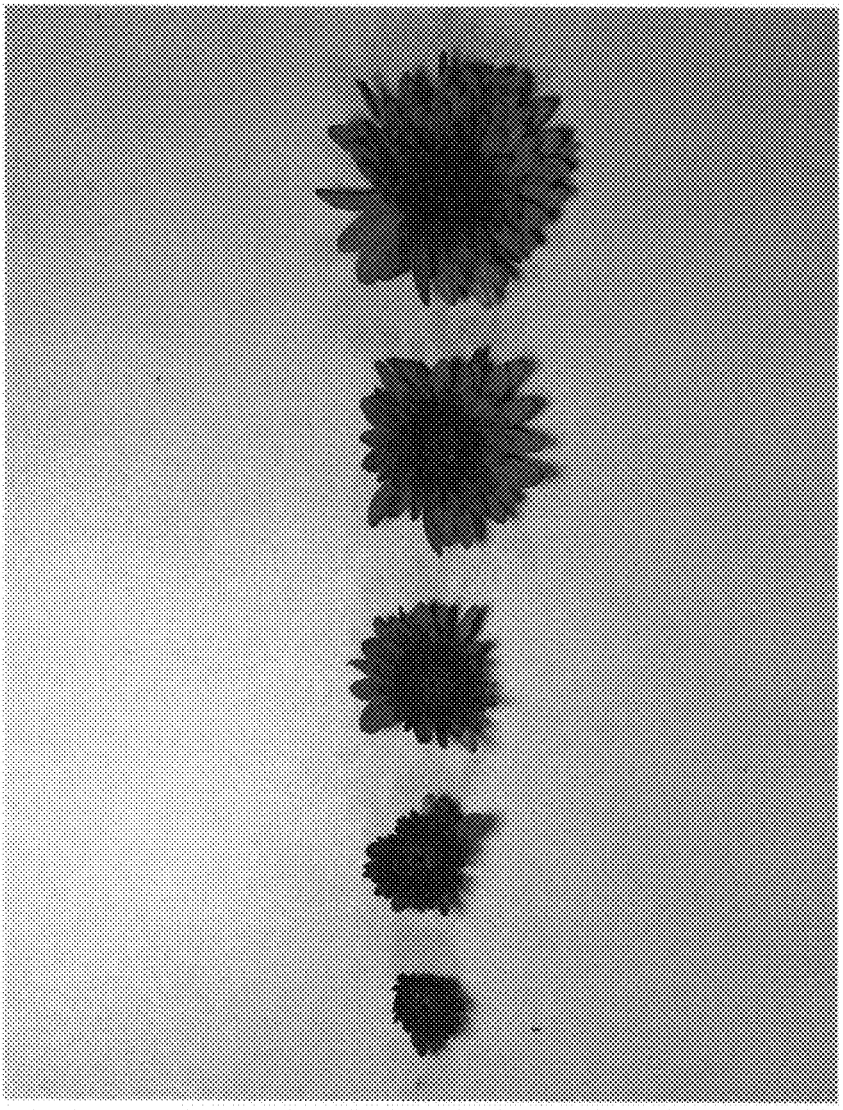
FIG. 2 shows the various stages of blooms of the new cultivar.
Figure 3:
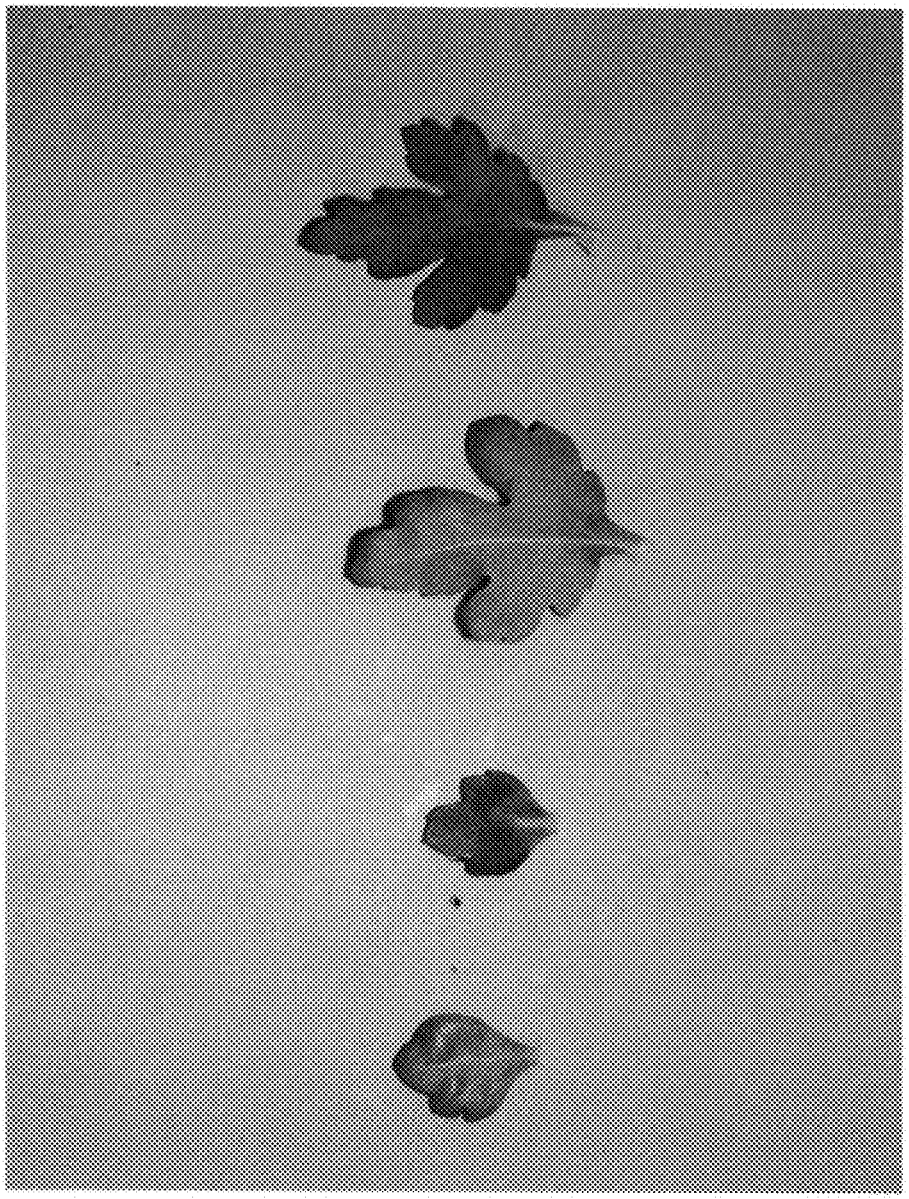
FIG. 3 shows the various stages of foliage of the new cultivar.

The observations and measurements were gathered from plants grown out door in Rijsenhout, The Netherlands, under natural day length and temperature and planted in week 22 in 2011. The natural blooming date of this crop was October 15 (week 42). The average height of the plants was 30 cm. No growth retardants were used. No tests were done on disease or insects resistance or susceptibility. No tests were done on cold or drought resistance. This new variety produces medium sized blooms with dark purple ray florets blooming for a period of five weeks.

From the cultivars known to inventor the most similar existing cultivar in comparison to 'Zanmuaval Purple' is its parent plant 'Zanmuaval' (U.S. Plant Pat. No. 22,659).

The following is a description of the plant and characteristics that distinguish 'Zanmuaval Purple' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour chart, edition 2001.

Detailed Botanical Description

Bud:

*Size.*—Small; cross-section 0.5 cm, height 0.3 cm.

*Shape.*—Oblate.

*Texture.*—Pubescent.

*Outside color.*—Greyed-green 191B.

Phyllaries:

*Number.*—20-22, arranged in 3 rows.

*Shape.*—Elliptic.

*Apex.*—Acute.
*Base.*—Truncate.
*Margin.*—Entire.
*Color.*—Upper surface: Greyed-green 191B. Lower surface: Green 138A.
*Length and width.*—1 cm; 0.1 cm.
*Texture.*—Pubescent.

Inflorescence:
*Type.*—Double.
*Height.*—1.5 cm.
*Diameter.*—5 cm.
*Peduncle length.*—5-6 cm.
*Peduncle color.*—Green 138C.
*Peduncle diameter.*—0.2 cm.
*Peduncle texture.*—Pubescent.
*Number per branch.*—Approx. 6 inflorescences.
*Duration of flowering.*—5 weeks.
*Seeds.*—Produced in small quantities, ovate, Greyed-brown 199A, length 1.5 mm, diameter 0.8 mm.
*Fragrance.*—Faint *chrysanthemum* odor.

Color:
*Center of inflorescences.*—Immature stage: Purple N77A. Mature stage: Purple N77A.
*Color of upper surface of the ray-florets.*—Purple N79B.
*Color of the lower surface of the ray-florets.*—Greyed-Purple 186C.
*Tonality from distance.*—A garden mum with dark purple flowers.
*Color of the ray-florets after aging of the plant.*—Purple N77D.

Ray florets:
*Texture.*—Upper and lower surface smooth.
*Number.*—240-260.
*Shape.*—Elliptic.
*Type.*—Predominantly ligulate.
*Apex.*—Varying from dentate to acute.
*Base.*—Attenuate.
*Cross-section.*—Flat.
*Longitudinal axis of majority.*—Straight.
*Length of corolla tube.*—0.3-0.4 cm.
*Ray-floret margin.*—Entire.
*Ray-floret length.*—1.5-2.3 cm.
*Ray-floret width.*—0.2-0.4 cm.
*Ratio length/width.*—High.

Disc florets: Absent.

Receptacle:
*Color.*—Green 138C.
*Shape.*—Conical raised.
*Height.*—0.4 cm.
*Diameter.*—0.4 cm.

Reproductive organs:
*Androecium.*—Absent.
*Pollen.*—Not produced.
*Gynoecium.*—Present in ray-florets.
*Style length.*—3 mm.
*Stigma color.*—Yellow 7A.
*Stigma width.*—1 mm.
*Ovary.*—Enclosed in calyx.

Plant:
*Form.*—Grown as a spray type pot mum, outdoor raised and mounded.
*Growth habit.*—Spherical shape.
*Growth rate.*—Medium.
*Height.*—30 cm.
*Width.*—50 cm.
*Stem color.*—Greyed-brown 199A.
*Stem strength.*—Weak.
*Stem brittleness.*—Brittle.
*Stem anthocyanin coloration.*—Present, streaks of Greyed-orange 177B.
*Internode length.*—2-4 cm.
*Length of lateral branch.*—From top to bottom 20 cm.
*Lateral branch color.*—Green 137 C.
*Lateral branch, attachment.*—Brittle.
*Lateral branch diameter.*—2 mm.
*Branching* (*average number of lateral branches*).—Prolific with 8-9 breaks after pinching.
*Natural season blooming date.*—October 17-21 (week 42).

Foliage:
*Leaf color.*—Upper side: Green 139A. Lower side: Green N138A.
*Color midvein.*—Upper side: Yellow-green 147D. Lower side: Yellow-green 148D.
*Size.*—Small; length 3-5 cm, width 2-3.5 cm.
*Quantity* (*number per lateral branch*).—15-17.
*Shape.*—Elliptic.
*Texture upper side.*—Sparsely pubescent.
*Texture under side.*—Pubescent.
*Venation arrangement.*—Palmate.
*Shape of the margin.*—Serrated.
*Shape of base of sinus between lateral lobes.*—Rounded.
*Margin of sinus between lateral lobes.*—Diverging.
*Shape of base.*—Truncate.
*Apex.*—Mucronulate.
*Petiole length.*—0.3-0.8 cm.
*Petiole diameter.*—0.2-0.4 cm.
*Petiole color.*—Yellow-green 147D.

TABLE 1

| Differences with the comparison varieties | | |
|---|---|---|
| Color upper surface ray-florets | 'Zanmuaval Purple' Purple N79B | 'Zanmuaval' Purple N79C |

I claim:

1. A new and distinct variety of *chrysanthemum* plant as described and illustrated.

* * * * *